(12) United States Patent
Zydney et al.

US007989615B2

(10) Patent No.: US 7,989,615 B2
(45) Date of Patent: Aug. 2, 2011

(54) SEPARATION OF DIFFERENT ISOFORMS OF PLASMID DNA USING ULTRAFILTRATION

(75) Inventors: Andrew Lawrence Zydney, State College, PA (US); David Robert Latulippe, St. George (CA)

(73) Assignee: The Penn State Research Foundation, University Park, PA (US)

( * ) Notice: Subject to any disclaimer, the term of this patent is extended or adjusted under 35 U.S.C. 154(b) by 318 days.

(21) Appl. No.: 12/217,777

(22) Filed: Jul. 9, 2008

(65) Prior Publication Data

US 2009/0018322 A1    Jan. 15, 2009

Related U.S. Application Data

(60) Provisional application No. 60/959,432, filed on Jul. 13, 2007.

(51) Int. Cl.
*C07H 21/04*    (2006.01)
(52) U.S. Cl. ..................................... 536/25.4
(58) Field of Classification Search ........................ None
See application file for complete search history.

(56) References Cited

U.S. PATENT DOCUMENTS

| | | | |
|---|---|---|---|
| 6,444,447 B1 * | 9/2002 | DeAngelis | 435/97 |
| 7,105,327 B1 * | 9/2006 | Kuppusamy et al. | 435/194 |
| 7,238,522 B2 * | 7/2007 | Hebel et al. | 435/306.1 |
| 7,285,651 B2 * | 10/2007 | Lander et al. | 536/23.1 |
| 7,604,973 B2 * | 10/2009 | DeAngelis | 435/193 |
| 7,767,399 B2 * | 8/2010 | Murphy et al. | 435/6 |

OTHER PUBLICATIONS

Varley et al., "Production of Plasmid DNA for Human Gene Therapy using Modified Alkaline Cell Lysis and Expanded Bed Anion Exchange Chromatography," Bioseparation, 8, 209-217 (1999).*
Latulippe, David R., et al., "Flux-dependent transmission of supercoiled plasmid DNA through ultrafiltration membranes," Journal of Membrane Science 294 (2007) 169-177.
Kong, Simyee et al., "Plasmid DNA processing for gene therapy and vaccination: Studies on the membrane sterilisation filtration step," Journal of Membrane Science 280 (2006) 824-831.
Hirasaki, Tomoko et al., "Permeation mechanism of DNA molecules in solution through cuprammonium regenerated cellulose hollow fiber (BMMtm)," Journal of Membrane Science 106 (1995) 123-129.

* cited by examiner

*Primary Examiner* — Lawrence E Crane
(74) *Attorney, Agent, or Firm* — Barbara E. Johnson, Esq.

(57) ABSTRACT

The invention is a method for isolating a desired plasmid DNA isoform, typically a supercoiled isoform, which includes the steps of obtaining a quantity of bioreactor produced plasmid DNA in liquid form for purification, and passing the plasmid DNA through an ultrafiltration membrane at a selected filtrate flux.

1 Claim, 13 Drawing Sheets

Table 1

| Feed (1) | Retentate (4) | Filtrate (5) |
|---|---|---|
| Linear, Supercoiled | Supercoiled | Linear |
| Linear, Open-Circular | Open-Circular | Linear |
| Supercoiled, Open-Circular | Open-Circular | Supercoiled |
| Linear, Supercoiled, Open-Circular | Supercoiled, Open-Circular | Linear |
| Linear, Supercoiled, Open-Circular | Open-Circular | Supercoiled, Linear |

Figure 3B

| Feed (1) | 1st Stage Retentate (4) | 2nd Stage Retentate (8) | 2nd Stage Filtrate (9) |
|---|---|---|---|
| Linear, Supercoiled, Open-Circular | Open-Circular | Supercoiled | Linear |

SEPARATION OF DIFFERENT ISOFORMS OF PLASMID DNA USING ULTRAFILTRATION

CROSS-REFERENCE TO RELATED APPLICATION

This specification claims priority to, and incorporates herein by reference, U.S. Provisional Application No. 60/959,432, filed Jul. 13, 2007.

BACKGROUND OF THE INVENTION

1. Field of the Invention

The invention pertains to novel methods of separating and purifying plasmid DNA isoforms using ultrafiltration.

2. Description of Related Art

There is considerable interest in using plasmids for gene therapy and DNA-based vaccines. These applications include: cancer (Allovectin-7®—Vical Inc.); cystic fibrosis (PLASmin™—Copernicus Therapeutics); hemophilia (Transkaryotic Therapies Inc.); and muscular dystrophy (MyoDys®—Transgene), among others.

Plasmids are circular, double-stranded extrachromosomal DNA that are produced by many bacteria in a plectonemic supercoiled form, often at high copy numbers. Large-scale production of plasmid DNA is performed in an appropriate bioreactor, with the plasmid released into the fluid medium by controlled cell lysis. One of the challenges in the preparation of a viable therapeutic product is the purification of the plasmid DNA, including removal of host cell proteins, genomic DNA, and RNA as well as the separation of the desired supercoiled isoform from the undesired linear and open-circular (i.e. nicked) isoforms. Current FDA guidelines recommend that at least 90% of the plasmid DNA in the final product must be in the supercoiled form. Therefore, the commercial need to obtain highly purified supercoiled plasmid DNA is extremely high.

For therapeutic applications, there is a particular and critical need for high purity product, which means that the bacterial host cell proteins, genomic DNA fragments, RNA, and endotoxins must all be removed. Moreover, the therapeutic effectiveness is dependent on the specific plasmid DNA morphology (i.e. isoform).

A variety of purification strategies have been examined for the large-scale separation of plasmid DNA including precipitation, aqueous two-phase separation, and also adsorption using monolithic columns. However, the dominant techniques used for the purification of plasmid DNA are chromatographic at this writing. These chromatographic techniques include size exclusion chromatography (SEC), anion exchange chromatography (AEX), hydrophobic interaction chromatography (HIC), and thiophilic-aromatic chromatography (TAC).

There are a number of challenges associated with the use of chromatographic systems for large-scale DNA purification. In particular, chromatographic processes suffer from many of the following limitations: limited resolution, low binding capacity, mass transfer limitations, and high process cost. For example, although HIC can provide reasonable separation of the open-circular and supercoiled forms, the separation between supercoiled and linear forms has heretofore been poor. Conflicting results have been reported for the use of AEX chromatography for DNA separation. Resolution of plasmid isoforms in SEC has been poor, and large-scale applications of SEC tend to be very time-consuming and expensive. Also, the pores of typical chromatographic resins are similar in size to plasmid DNA. Thus, much of the internal surface area of the resin is inaccessible to the DNA molecules and this in turn greatly increases the resin volume needed to purify the plasmid DNA.

Ultrafiltration is used extensively in bio-processing for the concentration and buffer exchange of therapeutic proteins, both for final product formulation and for pre-conditioning of feed streams prior to chromatography. Several previous studies have examined the potential of using ultrafiltration for the purification of plasmid DNA. Hirasaki et al., *J. Membr. Sci.*, 106: 123-129 (1995), in the only study to date that compared the UF transmission of different plasmid isoforms, found that the transmission of the linear isoform was slightly larger than that for the supercoiled form. However, the resolution was too low for effective separation. Kong et al., *J. Membr. Sci.*, 280: 824-831 (2006) investigated plasmid DNA transmission through microfiltration membranes and observed small differences in the overall rate of plasmid transmission depending upon the relative amount of the different isoforms, but no data were provided for the purification of the desired supercoiled form.

A need therefore remains for a technique for accurately and efficiently purifying specific plasmid DNA isoforms using a separation technique that is applicable for large-scale production of the desired isoform.

SUMMARY OF THE INVENTION

In order to meet this need, the present invention is a method of using pressure-driven ultrafiltration to purify the desired plasmid DNA isoform (typically the supercoiled isoform) by controlling the filtrate flux to exploit the effects of molecular flexibility on the transmission of the different plasmid isoforms. Separation is achieved by operating the ultrafiltration device at a filtrate flux (calculated as the volumetric filtration rate divided by the total membrane area) that is above the critical filtrate flux for transmission of one isoform and below the critical filtrate flux for transmission of the other isoform (s). The transmission of each DNA isoform is a strong function of the filtrate flux due to the elongation of the plasmid in the flow field at the entrance to the membrane pores. The plasmid DNA is almost completely rejected at low filtrate flux, with nearly complete transmission at a very high filtrate flux. The critical filtrate flux, $J_{crit}$, defined as the filtrate flux at which plasmid transmission first becomes significant, can be evaluated experimentally by extrapolating the transmission versus flux data to zero transmission. In theory, without intention of being bound thereby, the flux-dependence for the supercoiled, linear, and open-circular DNA are very different due to differences in elongational flexibility of the different DNA isoforms. The net result, regardless of dynamic, is that it is possible to purify the different isoforms by proper selection of the filtrate flux to control the extent of DNA transmission through the membrane. Operation at a filtrate flux between the critical flux values of the different isoforms allows one or more of the isoforms to be retained while the other isoform passes through the membrane. Purification of multiple isoforms can be achieved by operating sequentially at increasing values of the filtrate flux, possibly using multiple stage membrane cascades. The resolution of the DNA separation and required system operating conditions can be further improved by adjusting the membrane pore size and surface charge, the solution conditions (salt type and concentration), and temperature of the DNA solution, due—presumably—to the corresponding changes in the conformation and flexibility of the plasmid DNA.

BRIEF DESCRIPTION OF THE DRAWING(S)

FIGS. 6A and 6B show results for the separation of a linear 3.0 kbp plasmid from supercoiled and open-circular isoforms using a 300 kDa membrane.

FIGS. 7A and 7B show results for the separation of a supercoiled 3.0 kbp plasmid from open-circular isoform using a 100 kDa membrane.

FIGS. 8A and 8B show results for the separation of a linear 17.0 kbp plasmid from the supercoiled isoform using a 300 kDa membrane.

DESCRIPTION OF THE PREFERRED EMBODIMENT(S)

Figure 1:
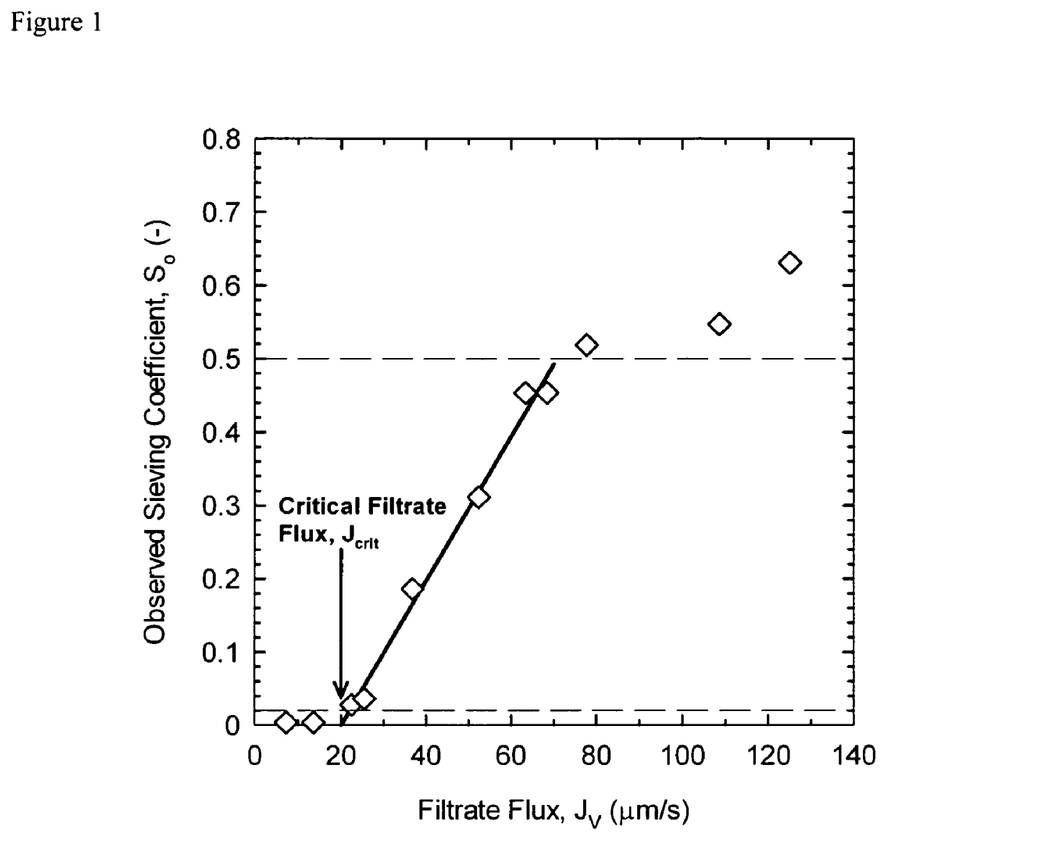
FIG. 1 is a graph showing the evaluation of the critical filtrate flux from a plot of the observed sieving coefficient, $S_o$ (defined as the ratio of plasmid concentration in the filtrate solution to plasmid concentration in the feed) as a function of the filtrate flux. The critical filtrate flux, $J_{crit}$, is evaluated by linear regression of the experimental data for $S_o$ values between about 0.02 and 0.5 (shown by dashed horizontal lines) followed by extrapolation of the linear fit to a zero value of the observed sieving coefficient. Experimental data were obtained with a 3.0 kilo base pair (kbp) supercoiled plasmid using a composite regenerated cellulose membrane with a nominal molecular weight cut-off (MWCO) of 300 kilo Dalton (kDa).

As summarized above and not repeated here, the present invention is a method of using pressure-driven ultrafiltration efficiently and effectively to filter and recover a desired isoform of plasmid DNA such as is created in bioreactors known in the art. The driving pressure, which controls the filtrate flux, is generally between 1-15 psig. The ultrafiltration membranes of the present invention are those well known in the art, typically having nominal molecular weight cut-offs between 100 and 1000 kDa. Separation is achieved by operating the filter at a filtrate flux that is between the critical flux for the desired isoform and that for the impurities (e.g., the less-desired isoforms), where the critical flux is evaluated by extrapolation of the sieving coefficient versus filtrate flux data to zero transmission as shown in FIG. 1.

Figure 4:
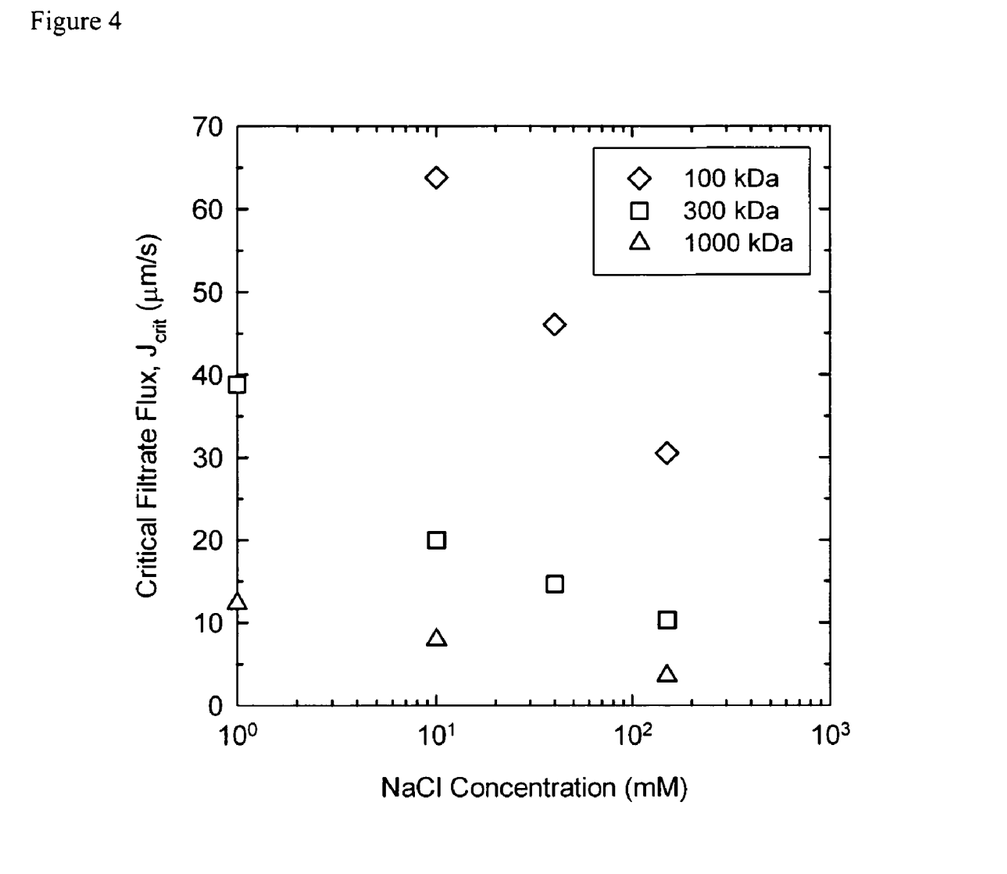
FIG. 4 is a graph showing the effect of salt (NaCl) concentration in the buffer solution on the critical filtrate flux for a 3.0 kbp supercoiled plasmid for three different membranes with different pore size as characterized by the molecular weight cut-off.
Figure 5:
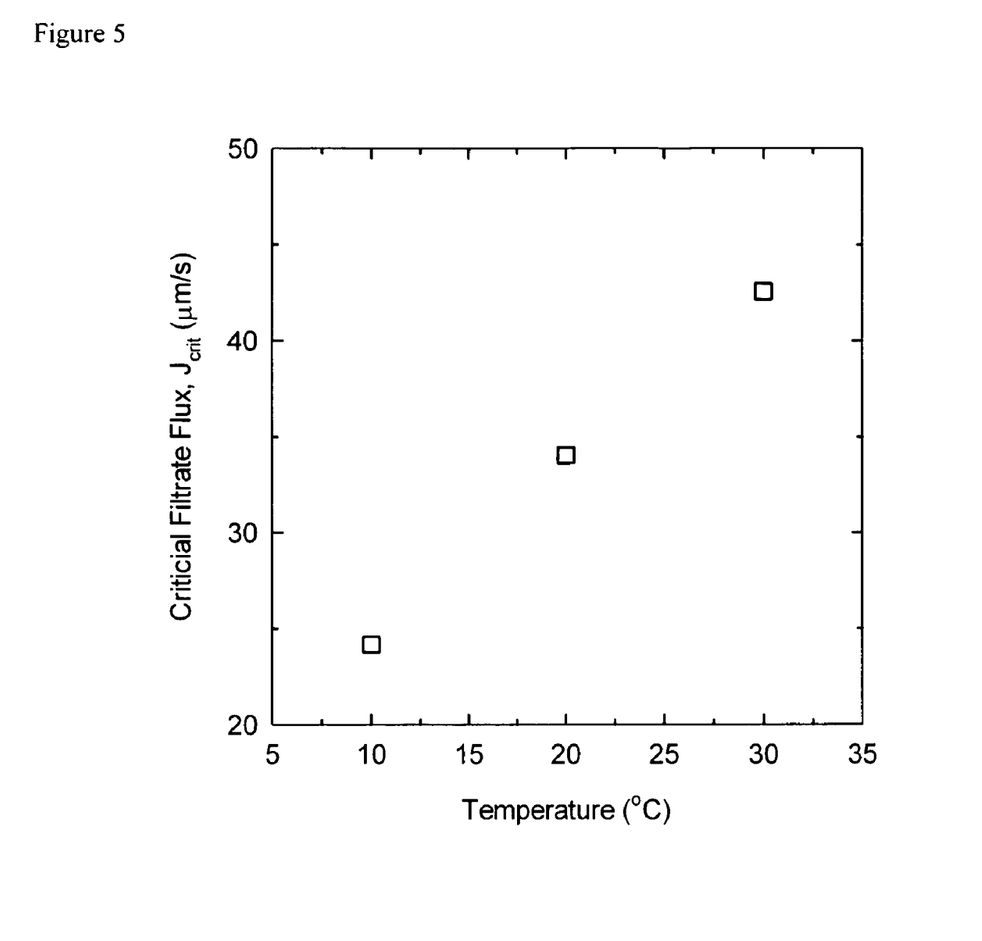
FIG. 5 is a graph showing the effect of solution temperature on the critical filtrate flux for a 3.0 kbp supercoiled plasmid using a 300 kDa membrane.

Although generally speaking the invention involves controlling the filtrate flux (through control of the driving pressure or through the use of a pump to directly control the filtration rate) through the ultrafiltration membrane to enhance recovery of the desired plasmid DNA isoform per se, additional features of condition control are also embraced by the present invention. For example, optimal membrane pore radius for the present ultrafiltration membranes is between 4-20 nm. Filtration rates are typically between 1-300 micrometers per second (µm/s), and more preferably between 10-150 micrometers per second. The presence of salt and temperature, as shown in FIGS. 4 and 5, respectively, can be used to control the value of the critical filtrate flux. It is also possible to use membranes with fixed electrical charge groups, for example, negatively-charged membranes made by attachment of specific acid groups to the base membrane. Given all the disclosure herein, one skilled in the art can create a filtration system to purify the plasmid isoform of interest while minimizing or avoiding the undesired DNA isoforms and other impurities.

Not only are the ultrafiltration membranes used in the present invention those known in the art, the DNA is generally filtered from buffers known in the art as well. The invention involves selecting the membrane pore size, surface charge density, temperature, and solution conditions to adjust the critical filtrate flux of each plasmid isoform and hence maximize recovery of the desired (typically supercoiled) plasmid DNA. As examples of these known membranes and buffers, in an experimental system used to confirm the assertions made herein, Ultracel™ composite regenerated cellulose membranes (Millipore) were used as follows. Membranes with molecular-weight cut-offs 100, 300, and 1000 kDa were cut into 25 mm disks and used in a stirred ultrafiltration cell. Other ultrafiltration systems are contemplated for use in the present invention, including the use of tangential flow filtration systems involving hollow fiber, cassette, or spiral wound modules. A diafiltration mode can also be employed to enhance the purification of the desired isoform. The Tris-EDTA buffer used was well known in the art; an exemplary 3.0 kbp pBluescript® plasmid and a 17.0 kbp plasmid, both prepared by Aldevron, were suspended in Tris-EDTA buffer prior to separation by the above-described regenerated cellulose membranes.

Examples of the above-described effects of filtrate flux, solution salt concentration, membrane pore size, and temperature on the ultrafiltration of plasmid DNA are shown in FIGS. 1, 2, 4, and 5.

The physical phenomena involved suggest deformation or elongation of the plasmid under the action of the pressure-driven filtration, although there is no intention of being bound by this theory. Empirically, however, there is significant plasmid transmission above a critical value of the filtrate flux even though the plasmid radius of gyration is greater than the membrane pore radius. For this reason, with respectively larger plasmid DNA (up to a minimum of 50 kbp), the invention does not require a proportional increase in membrane pore size. Also empirically, plasmid transmission increases at high flux and also increases at increased, or "high," salt concentrations, the latter effect of which suggests that the effective plasmid size decreases at high salt, which is consistent with AFM and light scattering measurements of plasmid size. The critical filtrate flux can be evaluated by extrapolation of a linear regression fit to experimental data for the plasmid sieving coefficient as a function of the filtrate flux to zero sieving coefficient as shown in FIG. 1.

It is also possible to estimate the critical filtrate flux for plasmid DNA theoretically using an elongational flow model. We note significant elongation when $De=\gamma^*\tau>1$, in which De is the Deborah number, $\tau$ is the time-scale for polymer relaxation, and $\gamma$ is the strain-rate for fluid flow. The free-draining model for polymer relaxation can be used to evaluate the time-scale for polymer relaxation:

$$\tau = \frac{R_G^2}{\pi^2 D}$$

in which $R_G$=plasmid radius of gyration and D=plasmid diffusion coefficient. The elongational flow into an isolated pore leads to the following equation for the strain-rate for fluid flow:

$$\gamma = \frac{r_p^2 J_v}{\varepsilon R_G^3}$$

in which $r_p$=membrane pore radius, $\varepsilon$=membrane porosity, and $J_v$=filtrate flux. The membrane pore radius can be estimated from the measured values of the membrane permeability, $L_p$ (water flow rate divided by membrane area divided by transmembrane pressure difference) as:

$$r_p = \left(\frac{8\eta\delta_m L_p}{\varepsilon}\right)^{1/2}$$

in which $\delta_m$ is the membrane thickness and $\eta$ is the solution viscosity. The critical filtrate flux for plasmid transmission can then be estimated by combining these equations with an expression for the plasmid diffusion coefficient as given by the Stokes-Einstein equation:

$$D = \frac{k_B T}{6\pi\eta\lambda R_G}$$

in which $k_B$ is the Boltzmann constant ($k_B=1.38\times10^{-23}$ J/K); T is the absolute temperature; and $\lambda$ is the ratio of the hydrodynamic radius of the plasmid ($R_H$) to the radius of gyration ($R_G$). The theoretical estimate of the critical filtrate flux, assuming significant elongation when De=1, is thus given as:

$$J_{crit} = \frac{\beta^3 \pi}{6}\left(\frac{1}{\lambda}\right)\left(\frac{\varepsilon}{r_p^2}\right)\left(\frac{k_B T}{\eta}\right)$$

where $\beta$ is approximately equal to 0.11 for a supercoiled plasmid.

To obtain high yields and purification factors, the separation should be accomplished in a diafiltration mode in which fresh buffer is continuously added to the feed solution as filtrate is removed through the membrane. This allows the more permeable isoform to be continually washed through the membrane while the more retained isoform is kept in the feed.

The plasmid of interest can be concentrated by performing an ultrafiltration at a filtrate flux below the critical flux for that isoform. The operating flux would typically be chosen at a value approximately 20% smaller than the critical flux.

Purification of the supercoiled plasmid from the open-circular and linear forms can be accomplished using a 2-step process since the critical flux for the supercoiled plasmid lies between the critical flux values of the other two isoforms. An initial ultrafiltration/diafiltration is performed at a filtrate flux between the critical flux values of the linear and supercoiled isoforms, with the linear isoform removed in the filtrate solution. A second ultrafiltration/diafiltration is then performed at a filtrate flux between the critical flux of the supercoiled and open-circular isoforms, with the supercoiled plasmid collected in the filtrate solution while the open-circular isoform is retained by the membrane.

Modes for Carrying Out the Invention

The separation system can be designed to selectively purify a desired plasmid isoform from a mixture containing two or more isoforms, including mixtures containing other impurities such as genomic DNA, host cell proteins, RNA, and endotoxins.

Figure 3A:
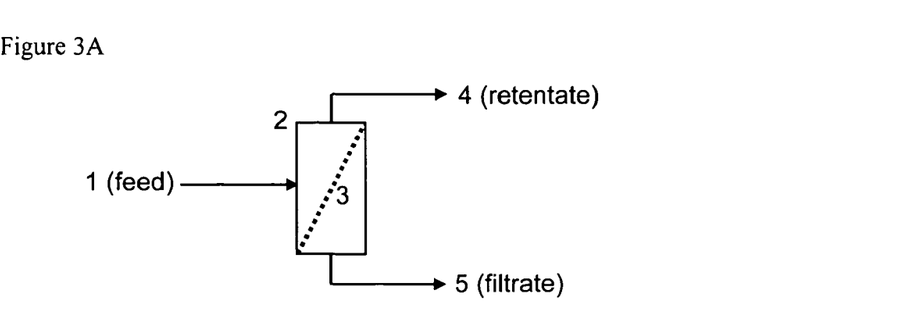
FIG. 3A depicts a schematic diagram of a single-stage apparatus for separating the supercoiled and linear isoforms. This single-stage device could also be used for purifying the supercoiled isoform from the linear and open-circular forms by operating the system sequentially with increasing filtrate flux, with the linear isoform removed in the filtrate at low flux and the supercoiled isoform collected in the filtrate solution after ultrafiltration at a higher flux. Other mixtures of the different plasmid DNA isoforms can be separated in a similar fashion as summarized in Table 1.

A single-stage ultrafiltration process is shown schematically in FIG. 3A. The mixture to be separated (stream 1) is typically fed from a feed tank through a pump that is connected directly to the ultrafiltration module (2) which contains the ultrafiltration membrane (3). The filtrate flux through the membrane is controlled by adjusting the transmembrane pressure or by a pump on the filtrate (stream 5) or retentate (stream 4) exits. The filtrate flux is chosen so that it lies between the values of the critical filtrate flux of the different isoforms. The plasmid isoforms that have critical flux values that are greater than the operating filtrate flux are selectively retained by the ultrafiltration membrane and leave the module via the retentate stream (4). The plasmid isoforms that have critical flux values that are smaller than the operating filtrate flux pass through the membrane and leave the filtration unit via the filtrate stream (5). Table 1 lists the different scenarios available to selectively purify a single isoform of plasmid DNA from binary or ternary mixture using this type of single-stage ultrafiltration process. A diafiltration can be performed by adding diafiltration buffer into the feed tank, typically at the same rate at which the filtrate is removed through the membrane thereby maintaining a constant volume in the feed tank.

Figure 3B:
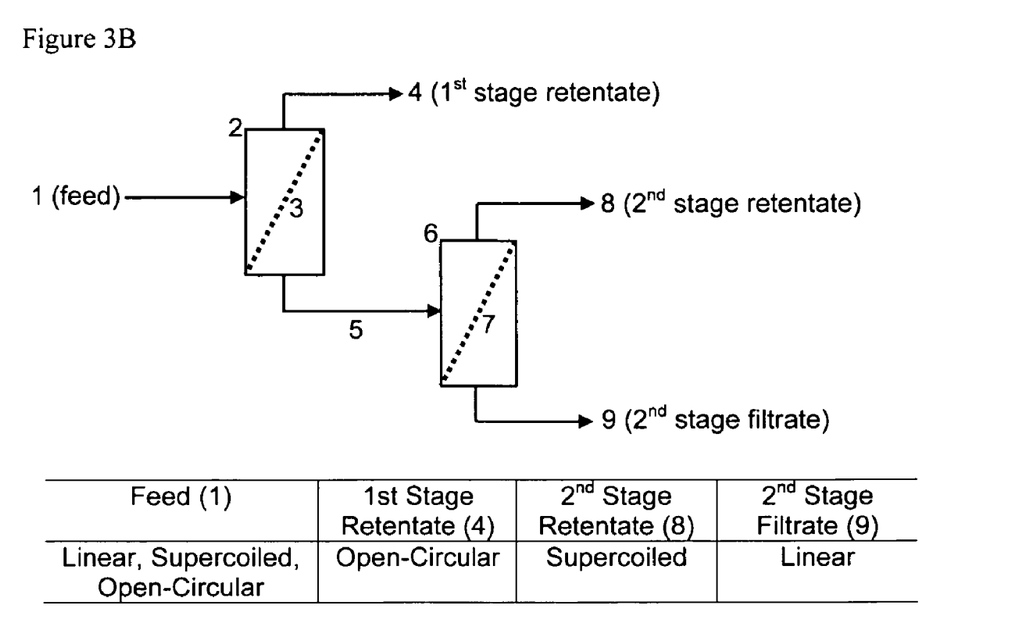
FIG. 3B depicts a two-stage apparatus for purifying supercoiled DNA from a feed solution containing the linear, supercoiled, and open-circular DNA isoforms. The first stage retains the open-circular isoform with the supercoiled and linear isoforms collected in the filtrate solution. The filtrate from the first-stage is fed to a second stage in which the supercoiled plasmid is collected in the retentate and the linear isoform is removed in the second filtrate.

The purification of a desired plasmid isoform can also be accomplished using the two-stage ultrafiltration process shown in FIG. 3B. The mixture to be separated (stream 1) is typically fed from a feed tank through a pump that is connected directly to the first-stage ultrafiltration module (2) which contains the ultrafiltration membrane (3). The filtrate flux through the membrane is controlled by adjusting the transmembrane pressure or by a pump on the filtrate (stream 5) or retentate (stream 4) exits. In the diagrammed mode of operation, the filtrate flux is maintained so that it lies between the values of the critical filtrate flux for the open-circular and supercoiled isoforms. Under these conditions, the open-circular isoform is selectively retained by the ultrafiltration membrane (3) and leaves the ultrafiltration module (2) via the retentate stream from the first stage (4). The linear and supercoiled isoforms pass through the ultrafiltration membrane (3) and leave the module via the filtrate stream (5). The fluid in stream 5 enters the $2^{nd}$ stage ultrafiltration module (6) which contains the ultrafiltration membrane (7). The ultrafiltration membrane in the second stage can have the same pore size (nominal molecular weight cut-off) as the ultrafiltration membrane in the first stage or it can be different. The filtrate flux in the second stage is maintained so that it lies between the values of the critical flux for the supercoiled and linear isoforms. Under these conditions, the purified supercoiled isoform is selectively retained by the ultrafiltration membrane (7) and leaves the ultrafiltration module (6) via the $2^{nd}$ stage retentate stream (8). The linear isoform passes through the ultrafiltration membrane (7) and is collected in filtrate stream 9. Both stages can be operated using a diafiltration mode, with diafiltration buffer added to the feed tank to continuously wash specific components through the membrane and into the filtrate solution.

Sample Protocol

The invention may be understood in view of a very specific protocol as provided and explained below.

Before any other step, the practice of the invention begins with a determination of which isoforms of plasmid DNA and what other impurities are present in the feed solution. Agarose gel electrophoresis (AGE) known in the art is one way to assess which plasmid isoforms are present. For plasmids that are between 3 and 20 kbp, AGE should be performed using 1.0 to 0.7% agarose gels (mass agarose/volume buffer) in electrophoresis buffer at applied voltages of 3-4 V/cm. Other methods available for analysis of the feed solution include high performance liquid chromatography (HPLC) and capillary gel electrophoresis (CGE). This step, of characterizing plasmid isoforms present in a feed solution, was known prior to the present invention, but should be performed as the first step of the novel separation of the invention.

As a second step, the practitioner should measure the transmission of the different plasmid isoforms in the feed solution (e.g., supercoiled, linear, and open-circular) through the ultrafiltration membrane as a function of the filtrate flux. Typical range of filtrate flux is 5 to 100 µm/s (corresponding to 18 to 360 L/m²/hr). For plasmids that are from 3 to 20 kbp, the ultrafiltration should be performed with an ultrafiltration membrane having a nominal molecular weight cut-off between 100 and 1000 kDa (pore size between approximately 5 and 20 nm), most probably using a membrane with a nominal molecular weight cut-off of 300 kDa. Concentrations of the different plasmids in the feed and filtrate solutions can be determined using an appropriate assay known in the art, including agarose gel electrophoresis, UV spectrophotometry, high performance liquid chromatography, or capillary gel electrophoresis.

Next, the practitioner evaluates the critical flux for each isoform of interest. The observed sieving coefficient is evaluated at each filtrate flux from the ratio of the plasmid isoform concentration in the filtrate solution to that in the feed solution. The observed sieving coefficient data are plotted as a function of the filtrate flux as shown in FIG. 1. The critical flux is determined by linear regression of the data with observed sieving coefficients between approximately 0.02 and 0.50 followed by extrapolation of the best linear fit to an observed sieving coefficient of zero as shown in FIG. 1. The different isoforms will have different critical flux due to differences in their flexibility. Initial estimates of the critical flux can be obtained using equations presented previously.

For each isoform, the critical flux can be adjusted according to the following guidelines: a) $J_{crit}$ decreases with increasing buffer salt concentration however, equivalent $J_{crit}$ values are achieved at lower concentrations of divalent cations salts (e.g. $MgCl_2$) compared to monovalent cation salts (e.g. NaCl); b) $J_{crit}$ decreases with decreasing operating temperature; c) $J_{crit}$ increases with increasing membrane surface charge density.

Next, the practitioner performs the desired isoform separation by operating the ultrafiltration device at a controlled filtrate flux that is between the critical flux values of the isoforms of interest. For example, the separation of the linear and supercoiled isoforms would be accomplished by operating the device at a filtrate flux that is larger than the critical flux for the linear isoform and smaller than the critical flux for the supercoiled isoform. The linear isoform would be collected in the filtrate while the supercoiled isoform would be collected in the retentate. The operating flux would typically be chosen at a value approximately 10-30% smaller than the critical flux of the supercoiled isoform. To obtain high yields and purification factors, the separation should be accomplished in a diafiltration mode in which fresh buffer is continuously added to the feed solution as filtrate is removed through the membrane. This allows the more permeable isoform to be continually washed through the membrane while the more retained isoform is kept in the feed.

The following examples illustrate the invention in further detail but are not intended to be limiting.

Example I

In this example, the separation of a linear 3.0 kbp plasmid from the supercoiled and open-circular isoforms was performed.

The 3.0 kbp pBluescript® plasmid was supplied by Aldevron at a concentration of 250 µg/mL in a predominantly (>90%) supercoiled form as determined by agarose gel electrophoresis (AGE). The linear isoform was prepared by enzymatic digestion: 110 µL of the supercoiled feed was mixed with 126.5 µL of deionized water, 27.5 µL of 10× React3 (Invitrogen), and 11 µL of BamHI (Invitrogen). The resulting mixture was incubated at 37° C. for 3 hours and then placed in a −20° C. freezer. The linear isoform was purified from the restriction enzyme using DNA Clean & Concentrator Kit (Zymo Research). The final concentration of the linear isoform was approximately 125 µg/mL.

The open-circular isoform was also prepared from the supercoiled pBluescript® plasmid by enzymatic digestion. 110 μL of the supercoiled plasmid solution was mixed with 132 μL of deionized water, 27.5 μL of 10× NE Buffer2 (New England BioLabs), and 5.5 μL of Nt.AlwI (New England BioLabs). The resulting mixture was incubated at 37° C. for 3 hours and then placed in a −20° C. freezer. The open-circular isoform was purified from the restriction enzyme using QIAQuick PCR Purification Kit (Qiagen). The final concentration of the open-circular isoform was approximately 125 μg/mL.

The Tris-EDTA (TE) buffer solution was prepared by diluting 10× Tris-EDTA solution (Sigma-Aldrich) and adding appropriate amount of sodium chloride (Sigma-Aldrich) to achieve 10 mM final concentration.

Solutions of the individual plasmid isoforms were prepared by adding 25 μg of the plasmid to TE buffer to obtain a final plasmid concentration of 250 ng/mL. Plasmid concentrations were determined using PicoGreen® nucleic acid stain (Invitrogen) according to the manufacturer's instructions using a fluorescent microplate reader.

Ultrafiltration experiments were conducting using 25 mm discs of 300 kDa Ultracel™ composite regenerated cellulose membrane (Millipore) housed within a 10 mL stirred cell (Millipore) with the filtration performed at room temperature, approximately 24° C.

Figure 2A:
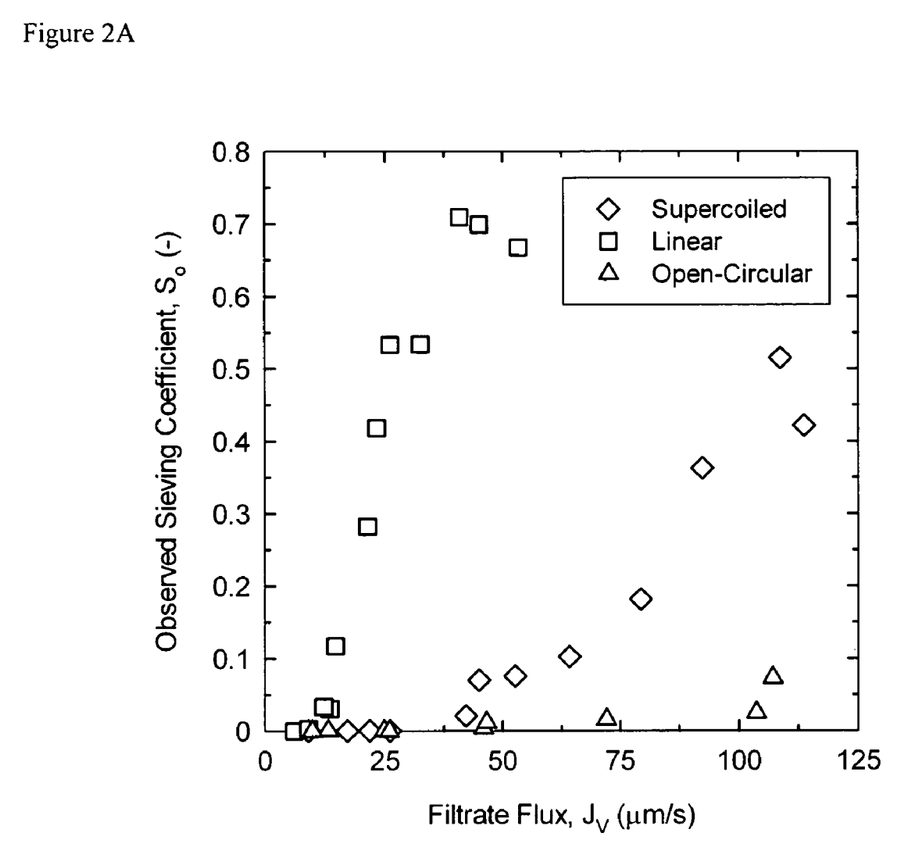
FIG. 2A is a graph showing the observed sieving coefficient as a function of filtrate flux for the three different plasmid isoforms: linear, supercoiled, and open-circular DNA for a 3.0 kbp plasmid through a 300 kDa nominal MWCO composite regenerated cellulose membrane.
Figure 2B:
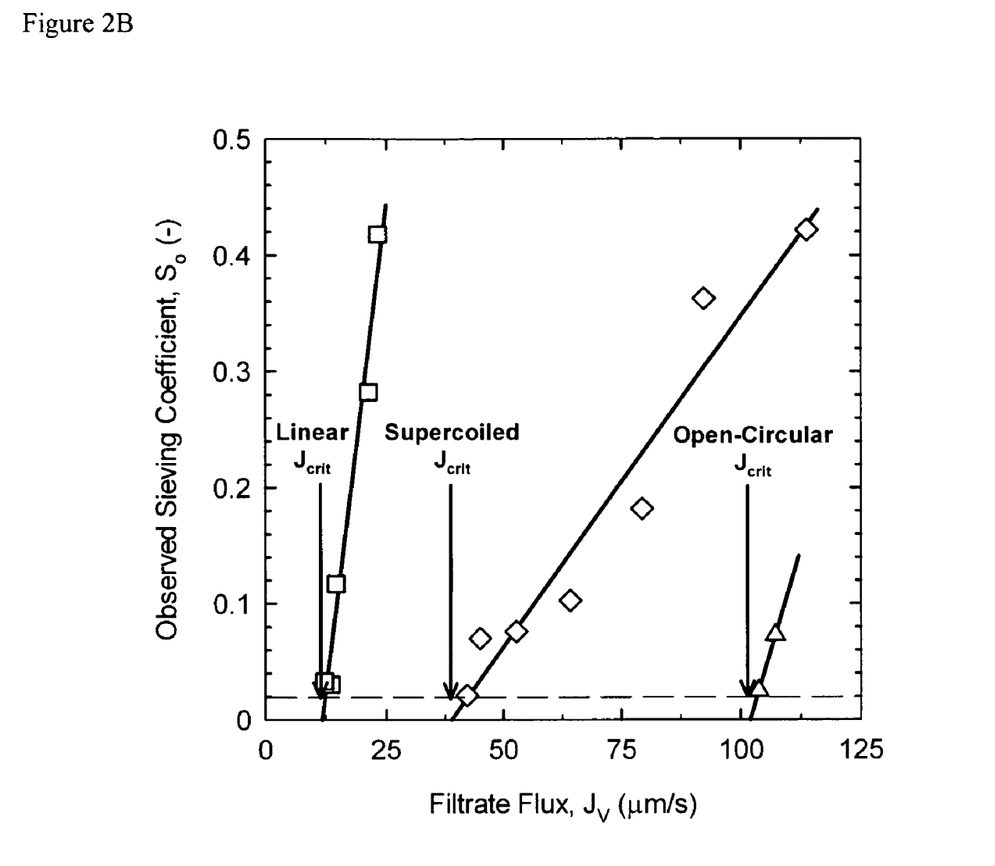
FIG. 2B shows the data from FIG. 2A used to calculate the critical filtrate flux for each plasmid isoform. The critical filtrate flux for the linear isoform is smaller than that for the supercoiled isoform which is in turn smaller than that for the open-circular (i.e. nicked) isoform.
Figure 6A:
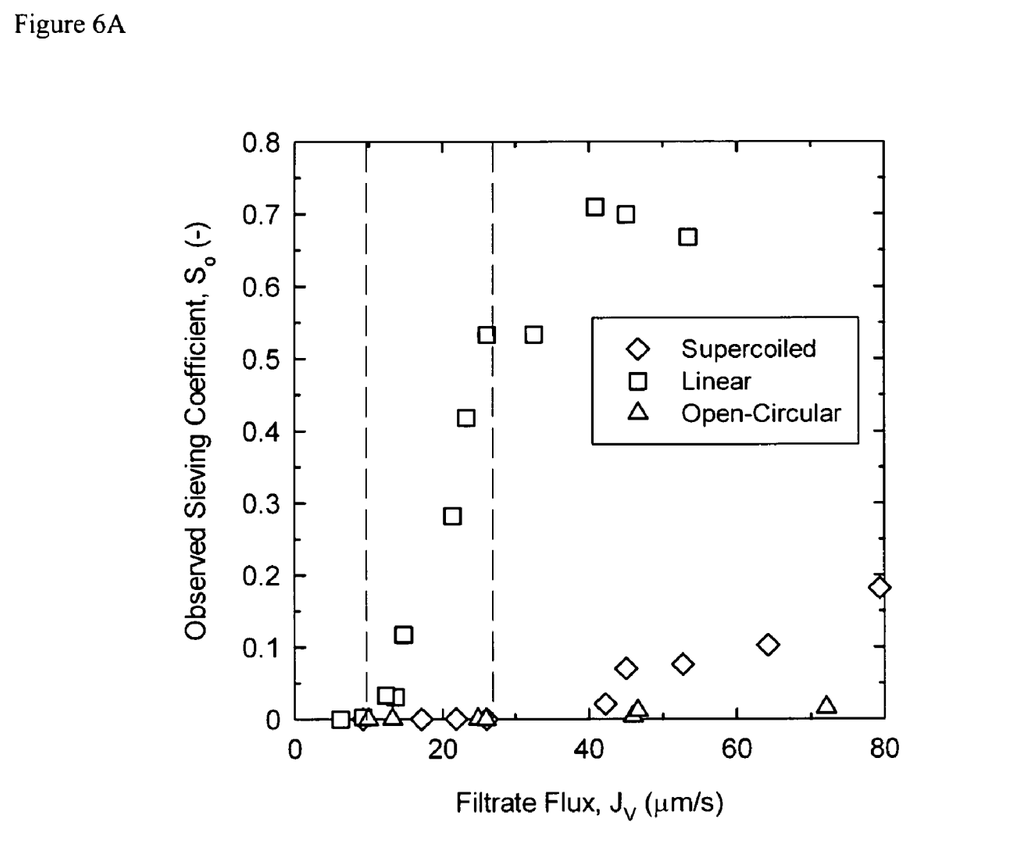
FIG. 6A shows data from experiments with single plasmid isoforms, with the vertical lines indicating the filtrate flux values appropriate for separation of a feed mixture containing the three isoforms.

The feed solution containing only a single plasmid isoform was added to the stirred cell and the device was air pressurized. The observed sieving coefficient was evaluated from the ratio of the plasmid concentration in the filtrate solution to that in the feed. Data were obtained over a range of filtrate flux from 6 to 115 μm/s obtained by adjusting the transmembrane pressure difference (by adjusting the air pressurization). Experimental results for the different plasmid isoforms are shown in FIG. 6A (same data set as shown in FIGS. 2A & 2B). The critical filtrate flux for each isoform was evaluated by linear regression of the sieving coefficient versus filtrate flux data followed by extrapolation of the linear fit to zero sieving coefficient. The filtrate flux identified by the dashed vertical lines in FIG. 6A would be appropriate for: (a) At 10 μm/s, the feed solution could be concentrated by ultrafiltration with all three plasmid isoforms retained by the membrane, and (b) At 27 μm/s, the linear isoform could be purified in the filtrate solution while the supercoiled and open-circular isoforms are retained by the membrane.

Figure 6B:
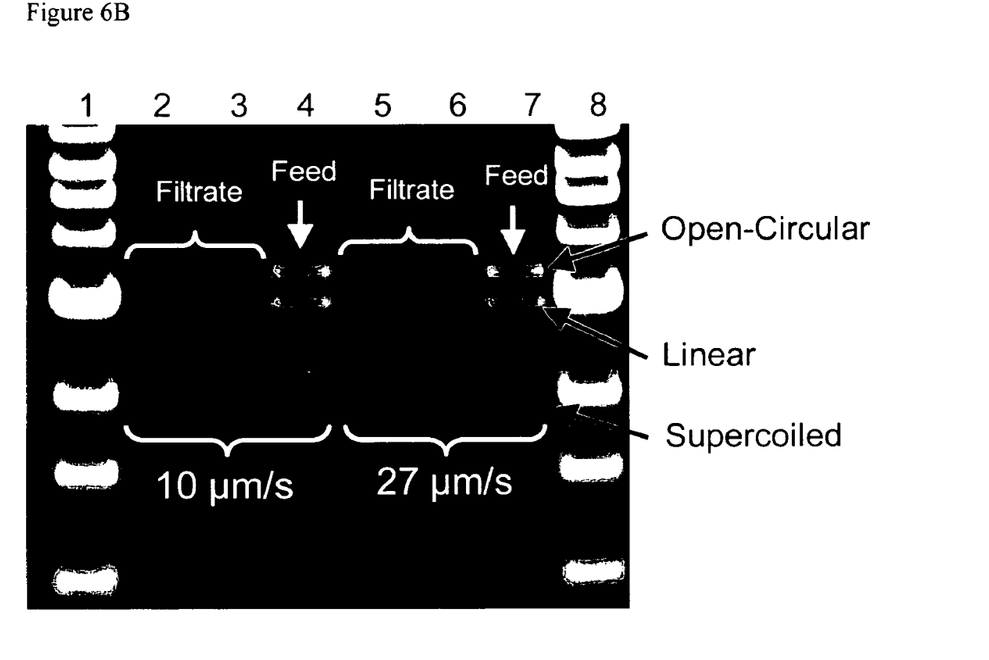
FIG. 6B shows an agarose gel electropherogram of filtrate and feed samples from the ultrafiltration experiment. At low filtrate flux (10 µm/s), all 3 isoforms are retained by the membrane allowing the feed to be concentrated. At the higher filtrate flux (27 µm/s) the linear isoform appears in the filtrate while the supercoiled and open-circular isoforms are retained by the membrane.

A mixture of the supercoiled, linear, and open-circular isoforms was prepared by mixing 25 μg of each isoform with TE buffer to obtain a total plasmid concentration of 750 ng/mL. Ultrafiltration was performed in two steps, first using a filtrate flux of 10 and then using a filtrate flux of 27 μm/s. Feed and filtrate samples were collected periodically throughout the ultrafiltration and analyzed as follows. The samples were concentrated approximately 12-fold using the QIAQuick PCR Purification Kit with 20 μL of the concentrated sample mixed with 4 μL of 6× TrackIT™ Loading Dye. Samples were loaded into wells of 1.0% agarose gel as follows: Lanes 1 and 8 contained 6 μL of 1 kb linear DNA ladder (New England BioLabs); Lanes 2 and 3 contained filtrate samples collected at filtrate flux of 10 μm/s; Lane 4 contained a feed sample obtained during the ultrafiltration performed at a filtrate flux of 10 μm/s; Lanes 5 and 6 contained filtrate samples collected at filtrate flux of 27 μm/s; Lane 7 contained a feed sample obtained during the ultrafiltration performed at filtrate flux of 27 μm/s. The gel was run at 4 V/cm for 160 minutes, stained with 120 mL of SyBr® Gold nucleic acid gels stain working solution for 18 hours, and then imaged using an AlphaImager® system (Alpha Innotech Corp.). FIG. 6B displays the image of the gel. The filtrate sample obtained at a filtrate flux of 10 μm/s shows no detectable levels of any of the plasmid isoforms. Operation at this filtrate flux would be ineffective for plasmid purification, although these conditions would be suitable for concentration of the feed solution. The filtrate sample obtained at a filtrate flux of 27 μm/s shows high levels of the linear isoform while there was no evidence of any significant amounts of the supercoiled or open-circular isoforms. Thus, operating the ultrafiltration device at a filtrate flux above the critical flux for the linear isoform and below the critical flux for the supercoiled and open-circular isoforms provided a filtrate solution that contained the purified linear plasmid isoform.

Example II

In this example, the separation of a supercoiled 3.0 kbp plasmid from the open-circular isoform was performed.

The supercoiled and open-circular isoforms were prepared as detailed in Example I. The buffer solution was prepared by diluting 10× Tris-EDTA solution (Sigma-Aldrich) and adding appropriate amount of sodium chloride (Sigma-Aldrich) to achieve 150 mM final concentration.

Solutions of the individual plasmid isoforms were prepared by adding 25 μg of the plasmid to TE buffer to obtain a final plasmid concentration of 250 ng/mL. Plasmid concentrations were determined using PicoGreen® nucleic acid stain (Invitrogen) according to the manufacturer's instructions using a fluorescent microplate reader.

Ultrafiltration experiments were conducting using 25 mm discs of 100 kDa Ultracel™ composite regenerated cellulose membrane (Millipore) housed within a 10 mL stirred cell (Millipore) with the filtration performed at room temperature, approximately 24° C.

Figure 7A:
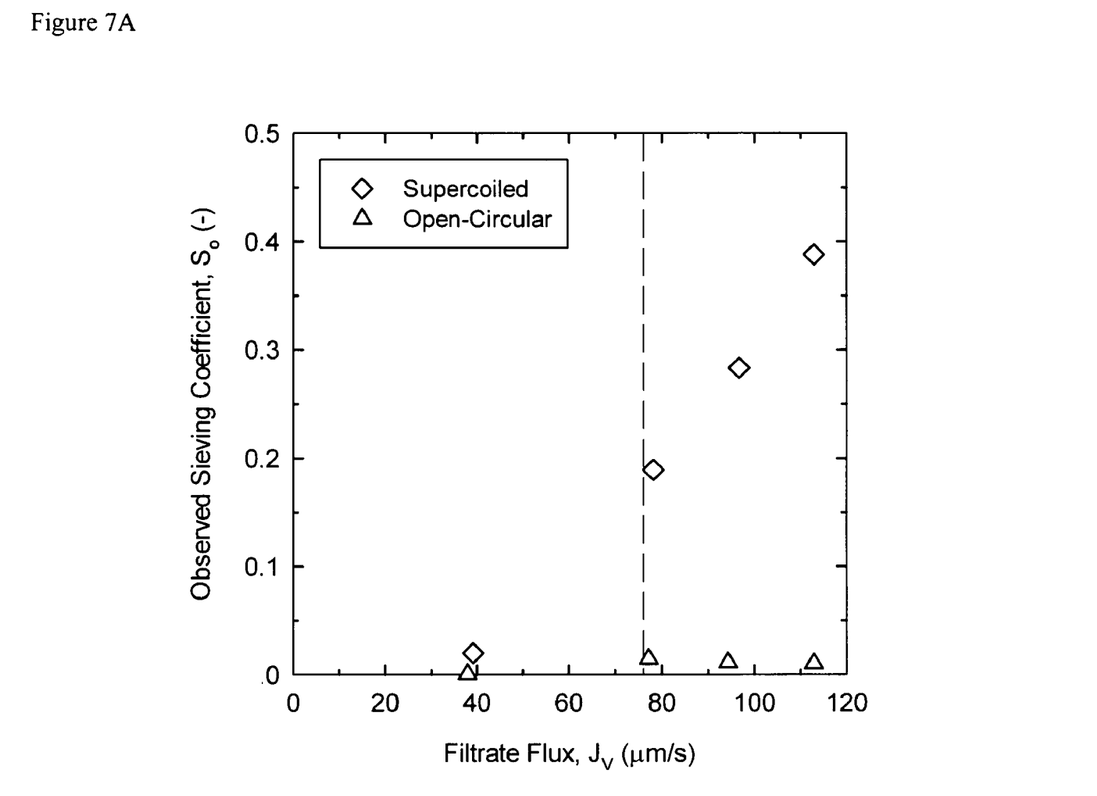
FIG. 7A shows data from experiments with single plasmid isoforms, with the vertical line indicating the filtrate flux value appropriate for separation of the feed mixture containing the two isoforms.

The feed solution containing only a single plasmid isoform was added to the stirred cell and the device was air pressurized. The observed sieving coefficient was calculated over a range of filtrate flux from 35 to 115 μm/s. The data for each plasmid isoform are shown in FIG. 7A. The critical filtrate flux was evaluated by linear regression of the sieving coefficient versus filtrate flux data followed by extrapolation of the linear fit to zero sieving coefficient. The filtrate flux identified by the dashed vertical line in FIG. 7A was identified as being appropriate for collection of the supercoiled isoform in the filtrate solution while retaining the open-circular isoform by the membrane.

Figure 7B:
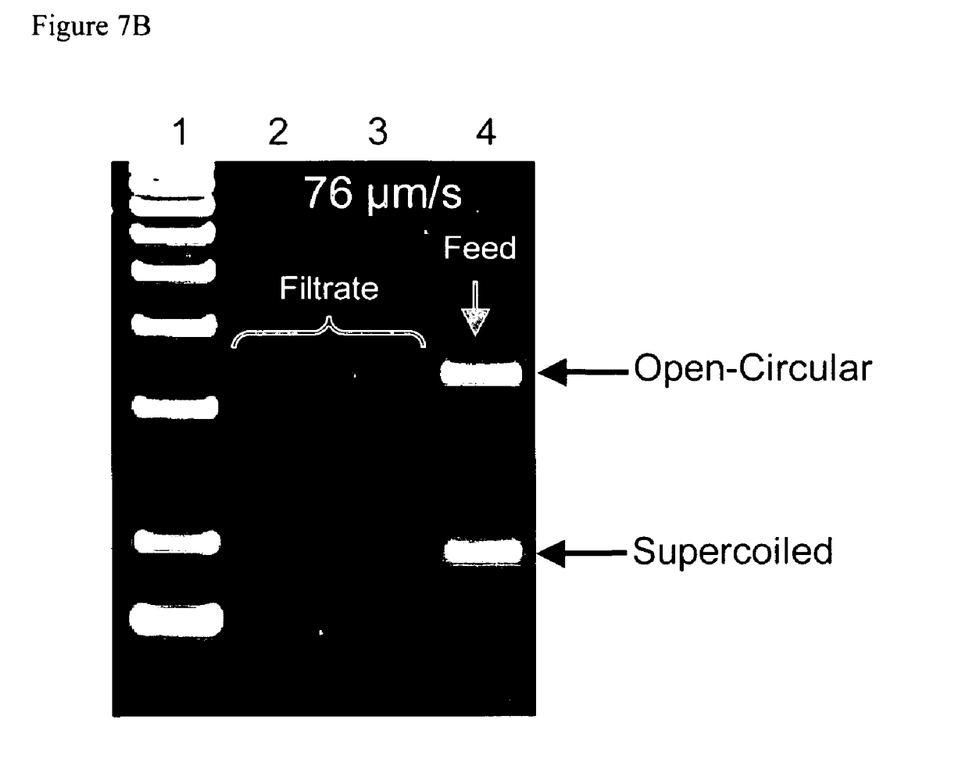
FIG. 7B displays an agarose gel electropherogram of filtrate and feed samples from the ultrafiltration experiment. The purified supercoiled isoform is collected in the filtrate while the open-circular isoform is retained by the membrane.

A mixture of the supercoiled and open-circular isoforms was prepared by mixing 25 μg of each isoform with TE buffer to obtain a total plasmid concentration of 500 ng/mL. Ultrafiltration was conducted at a filtrate flux of 76 μm/s. Feed and filtrate samples were collected periodically throughout the ultrafiltration and analyzed as follows. The samples were concentrated (5-fold for feed, 15-fold for the filtrate) using the QIAQuick PCR Purification Kit with 20 μL of the concentrated sample mixed with 4 μL of 6× TrackIT™ Loading Dye. Samples were loaded into wells of 1.0% agarose gel as follows: Lane 1 contained 6 μL of TrackIT™ 1 kb linear DNA ladder (Invitrogen); Lanes 2 and 3 contained filtrate samples collected at a filtrate flux of 76 μm/s; Lane 4 contained a feed sample obtained during the ultrafiltration at a filtrate flux of 76 μm/s. The gel was run at 4 V/cm for 175 minutes, stained with 120 mL of SyBr® Gold nucleic acid gels stain working solution for 18 hours, and then imaged using an AlphaImager® system (Alpha Innotech Corp.). FIG. 7B displays the image of the gel. The filtrate sample shows a high concentration of the supercoiled isoform with only trace amounts of the open-circular isoform. Thus, by operating the ultrafiltration device at a filtrate flux above the critical flux for the supercoiled isoform and below the critical flux for the open-circular isoform it was possible to separate these two isoforms, producing a filtrate solution that contained the purified supercoiled isoform.

Example III

In this example, the separation of a linear 17.0 kbp plasmid from the supercoiled isoform was performed.

The 17.0 kbp plasmid, generated by insertion of a 14.0 kbp fragment into the NotI site of the pBluescript® vector, was supplied by Aldevron at a concentration of 250 µg/mL in a predominantly (>90%) supercoiled form as determined by AGE.

The linear isoform was prepared by enzymatic digestion: 110 µL of the supercoiled feed was mixed with 123.75 µL of deionized water, 27.5 µL of 10× NE Buffer2 (New England BioLabs), 2.75 µL of 100× BSA (New England BioLabs), and 11 µL of XhoI (New England BioLabs). The resulting mixture was incubated at 3° C. for 3 hours and then placed in a −20° C. freezer. The plasmid isoform was purified from the restriction enzyme using DNA Clean & Concentrator Kit (Zymo Research). The final concentration of the linear isoform was approximately 120 µg/mL. The buffer solution was prepared by diluting 10× Tris-EDTA solution (Sigma-Aldrich) and adding appropriate amount of sodium chloride (Sigma-Aldrich) to achieve 10 mM final concentration.

Solutions of the individual plasmid isoforms were prepared by diluting 24-25 µg of the plasmid with TE buffer to obtain a final plasmid concentration of 240-250 ng/mL. Plasmid concentrations were determined using PicoGreen® nucleic acid stain (Invitrogen) according to the manufacturer's instructions using a fluorescent microplate reader.

Ultrafiltration experiments were conducting using 25 mm discs of 300 kDa Ultracel™ composite regenerated cellulose membrane (Millipore) housed within a 10 mL stirred cell (Millipore) with the filtration performed at room temperature, approximately 24° C.

Figure 8A:
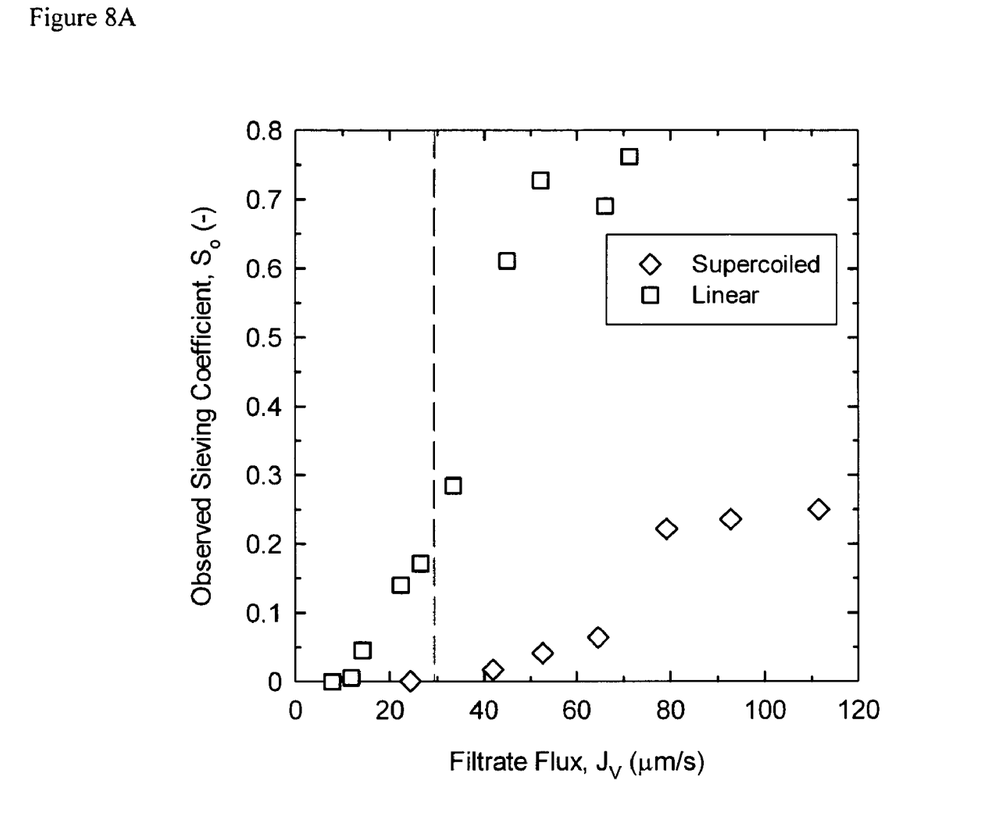
FIG. 8A shows data from experiments with single plasmid isoforms, with the vertical line indicating the filtrate flux value appropriate for separation of the feed mixture containing the two isoforms.

The feed solution containing only a single plasmid isoform was added to the stirred cell and the device was air pressurized. The observed sieving coefficient was calculated over a range of filtrate flux from 7 to 115 µm/s. The data for each plasmid isoform are shown in FIG. 8A. The critical filtrate flux was evaluated by linear regression of the sieving coefficient versus filtrate flux data followed by extrapolation of the linear fit to zero sieving coefficient. The filtrate flux identified by the dashed vertical line in FIG. 8A would be appropriate for the collection of the linear isoform in the filtrate solution while the supercoiled is retained by the membrane.

Figure 8B:
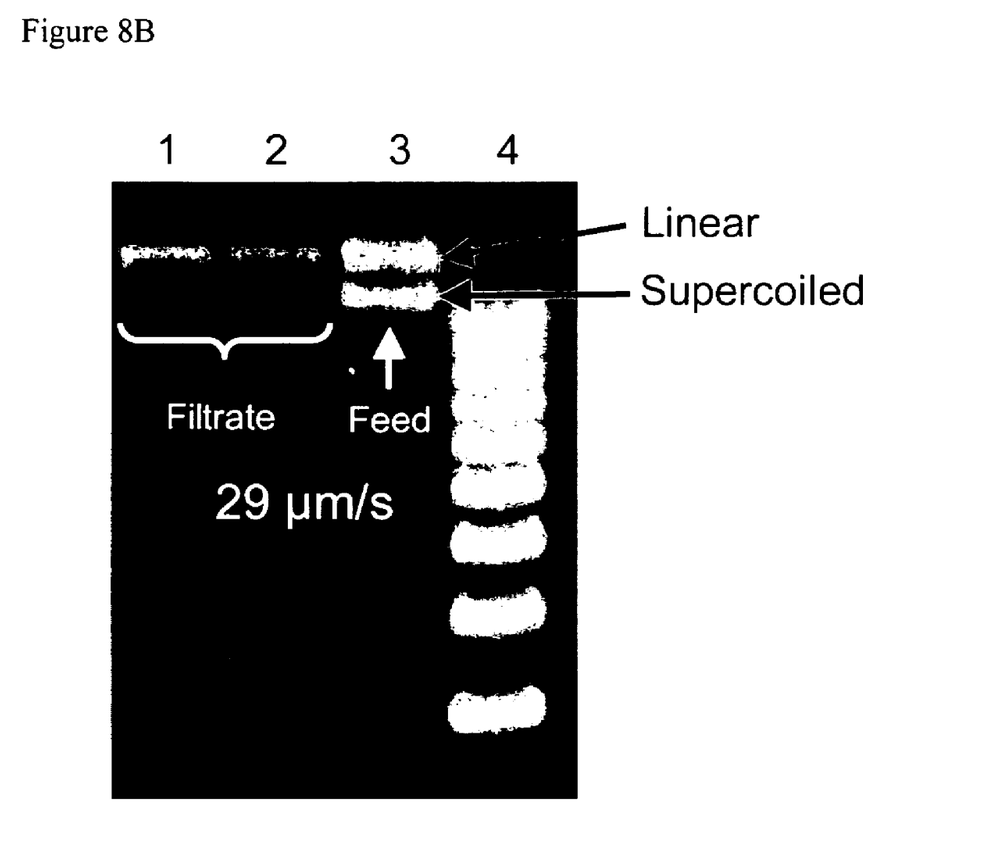
FIG. 8B displays an agarose gel electropherogram of filtrate and feed samples from the ultrafiltration experiment. The linear isoform appears in the filtrate while the supercoiled isoform is retained by the membrane.

A mixture of the supercoiled and linear isoforms was prepared by mixing 25 µg of each isoform with TE buffer to obtain a total plasmid concentration of 500 ng/mL. Ultrafiltration was conducted at a filtrate flux of 29 µm/s. Feed and filtrate samples were collected periodically throughout the ultrafiltration and analyzed as follows. The samples were concentrated (5-fold for feed, 14-fold for the filtrate) using the DNA Clean & Concentrator Kit with 20 µL of the concentrated sample mixed with 4 µL of 6× TrackIT™ Loading Dye. Samples were loaded into wells of 0.7% agarose gel as follows: Lanes 1 and 2 contained filtrate samples collected at a filtrate flux of 29 µm/s; Lane 3 contained a feed sample obtained during the ultrafiltration at a filtrate flux of 29 µm/s; Lane 4 contained 6 µL of TrackIT™ 1 kb linear DNA ladder (Invitrogen). The gel was run at 3.6 V/cm for 240 minutes, stained with 120 mL of SyBr® Gold nucleic acid gels stain working solution for 18 hours, and then imaged using an AlphaImager® system (Alpha Innotech Corp.). FIG. 8B displays the image of the gel. The filtrate sample obtained at a filtrate flux of 29 µm/s shows high levels of the linear isoform while there was no evidence of any significant amounts of the supercoiled isoform. Thus, operating the ultrafiltration device at a filtrate flux above the critical flux for the linear isoform and below the critical flux for the supercoiled isoform provided a filtrate solution that contained the purified linear plasmid isoform.

Although the invention has been described herein with particularity, the invention is only to be considered to be limited insofar as is set forth in the accompanying claims.

The invention claimed is:

1. A method for isolating a plasmid DNA isoform selected from the group consisting of linear plasmid isoforms, open-circular plasmid isoforms and supercoiled plasmid isoforms, comprising: obtaining a quantity of bioreactor produced plasmid DNA in liquid form; passing said quantity of liquid, in a closed system, through an ultrafiltration membrane having a nominal molecular weight cut-off between 100-1000 kDa (corresponding to pore size between approximately 4 and 20 nm) for plasmids that are from 3 to 50 kbp in size at a filtrate flux between 1-300 micrometers per second; and recovering said plasmid DNA isoform in purified form from the ultrafiltration procedure thus described.

* * * * *